United States Patent [19]

Edwards

[11] 4,369,769
[45] Jan. 25, 1983

[54] SPINAL FIXATION DEVICE AND METHOD

[76] Inventor: Charles C. Edwards, 3907 Greenway, Baltimore, Md. 21218

[21] Appl. No.: 159,396

[22] Filed: Jun. 13, 1980

[51] Int. Cl.³ ............................................. A61F 5/01
[52] U.S. Cl. .................................................... 128/69
[58] Field of Search .................. 128/69, 75, 78, 84 R, 128/84 C, 92 R, 92 B–92 BC

[56] References Cited

U.S. PATENT DOCUMENTS

| | | |
|---|---|---|
| 3,367,326 | 2/1968 | Frazier . |
| 3,426,364 | 2/1969 | Lumb . |
| 3,596,656 | 8/1971 | Kaute ............................. 128/92 BA |
| 3,741,205 | 6/1973 | Markolf ............................ 128/92 B |
| 3,961,854 | 6/1976 | Jaquet . |
| 4,078,559 | 3/1978 | Nissinen . |
| 4,085,744 | 4/1978 | Lewis ................................... 128/75 |
| 4,269,178 | 5/1981 | Keene ................................... 128/69 |

FOREIGN PATENT DOCUMENTS 662082  5/1979  U.S.S.R. .......................... 128/92 BC

OTHER PUBLICATIONS

Zimmer Catalog, Harrington Instrumentation, Zimmer Industries, Warsaw, Indiana, 1973.

Primary Examiner—Richard J. Apley
Assistant Examiner—Carl Moy
Attorney, Agent, or Firm—Sherman & Shalloway

[57] ABSTRACT

A spinal fixation device in which sleeves or spacers are placed over or around spinal rods in order to obtain better reduction of spinal fractures or spinal deformities. The sleeves can be made in various thicknesses so that the surgeon can obtain optimum fixation in each case. The sleeves can be made of any biologically compatible material.

17 Claims, 6 Drawing Figures

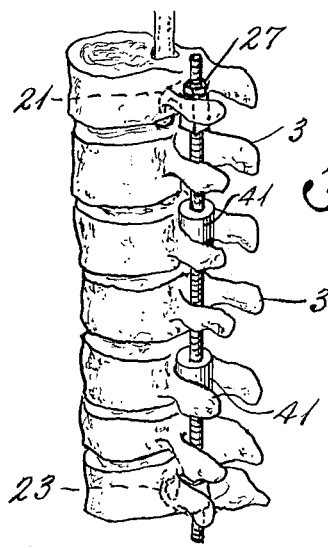
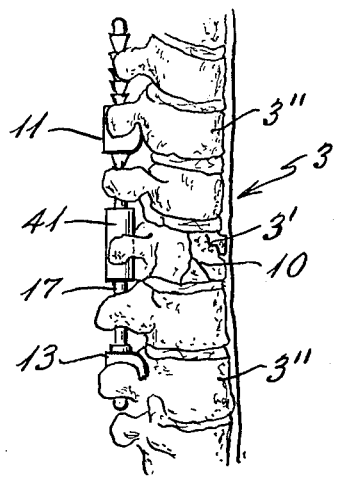
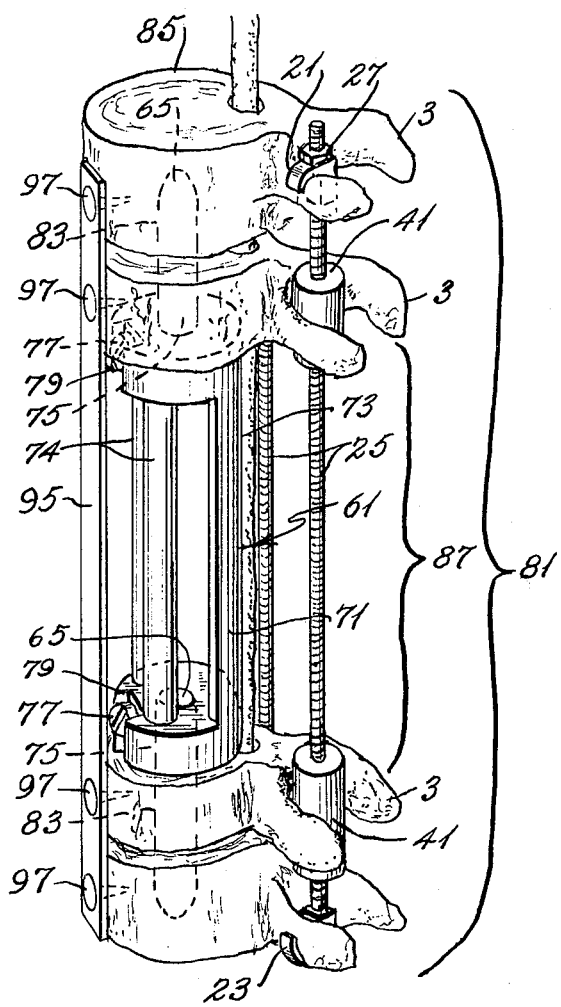

SPINAL FIXATION DEVICE AND METHOD

BACKGROUND OF THE INVENTION

1. Field of the Invention

This invention relates to a surgically implanted spinal fixation device and method which permits improved correction of deformity and provides increased stability in the fixation of spinal fractures and other spinal deformities such as scoliosis and kyphosis.

2. Discussion of the Prior Art

The prior art includes a number of devices for use in correction of spinal deformities. Such devices are illustrated in U.S. Pat. Nos. 3,367,326; 3,426,364; 3,961,854 and 4,078,559, for example. One prior art device, disclosed in U.S. Pat. No. 3,426,364 uses a Y-shaped element which is connected to a body forming portion in order to replace one or more natural vertebrae.

Prior art devices have been used primarily for the correction of lateral deviation of the spinal column, known as scoliosis. The spinal curvature which results from scoliosis is generally defined on the basis of specific reference points. In particular, the extreme upper and lower vertebrae and the most displaced vertebra are of particular interest. The extreme upper and lower vertebrae are those which are the most inclined relative to the median longitudinal axis of the torso. The two planes within which the extreme upper and lower vertebrae can be found define the scoliotic angle. The most displaced, or apical, vertebra is defined as the vertebra which is the farthest from the median axis of the torso.

However, it is during surgery that the correction is completed and finalized. For this purpose, a solid rod with anchoring hooks is typically placed in the concavity of the curvature and a threaded rod with hooks is placed on the convexity of the curvature. These rods straighten the spine and maintain the correction until arthrodesis is attained by means of autogenous bone graft. The implants used most often to correct curvature during surgery are known as the Harrington TM distraction system and the Harrington TM compression system. Harrington is a trademark of Zimmer U.S.A., Inc., Warsaw, Ind.

Another use for spinal rods is correction of Kyphotic (hunchback) deformities produced by disease or spinal injury. In this use, the compression or distraction rods are used. Correction can be achieved by pushing the lamina of the apical vertebra anteriorly with the rods. However, particularly where the spine has a neutral or lordotic curve, there is a gap between the rods and spinal laminae. To the extent of this gap the spinal deformity cannot be reduced in such a way as to restore or maintain anatomic lumbar lordosis, and full indirect spinal cord decompression often cannot be achieved. Moreover, since the anterior longitudinal ligament and other soft tissues attached to the vertebrae anteriorly are not placed under maximal stress in such a case, maximum stability of fixation is not accomplished either.

Improved three-point fixation can be achieved by bending of such rods. However, clinical experience has shown that despite wire and other methods of splinting the bent rods, they can rotate out of position.

One prior art solution to the problem of bent rods rotating out of position has been to use square hole hooks and rods. The use of square hole hooks and rods has four disadvantages, however:

1. A hospital is required to double its stock of rod equipment;
2. The bending technique weakens the rod;
3. The technique requires considerable time and skill to obtain the ideal amount and location of the bend during surgery;
4. Many rods can be wasted in achieving the ideal bend during the operation.

Thus, the prior art devices do not provide for spine stabilizing devices which provide enhanced pressure distribution against the spinal vertebrae, high stability against rotation, or easily convertible dimensioning to accommodate differently sized patients and patterns of spinal injury or deformity.

OBJECTS AND SUMMARY OF THE INVENTION

Therefore, an object of the present invention is to provide an improved spinal rod assembly overcoming the aforementioned prior art problems.

A further object of the invention is to provide increased stability in the reduction and fixation of spinal fractures and other spinal deformities including rotational stability achieved by providing contact with the spinous process, medially, and the facets, laterally.

Another object of the invention is to provide stress distributing elements for the use with spinal fixation devices.

Still another object of the invention is to provide sleeves, or spacers, for use with spinal rods to provide an appropriate fit between the rod and spine and, hence, achieve greater anterior or lateral pressure over the apical vertebra with greater correction of both kyphotic and rotatory deformity.

It is yet another object of the invention to provide such sleeves which are quickly and simply insertable during a surgical procedure and fully adjustable along a spinal rod as to point of boney contact and/or pressure.

Another object of the invention is to indirectly relieve pressure from the spinal cord in cases where bone from a fractured vertebral body is impinging on the cord. This may be accomplished by three mechanisms:

1. Posteriorly displaced bone fragments from the vertebral body are pushed, anteriorly, away from the cord by the vertebral pedicals which are, in turn, pushed foward by the sleeves;
2. Increased local lordosis is produced; by the sleeves pushing forward on the posterior elements of the apical vertebrae; this advances fractured vertebral bone anteriorly away from the cord; and,
3. Bone fragments attached to spinal ligaments may be pulled away from the cord because the sleeve can impart superior local distractive forces across the injured segment by providing greater lordosis and, hence, permitting more distractive force than present systems.

Another object where sleeves are used with distraction rods is to permit greater distraction of the rods in order to lessen the incidence of subsequent hook or rod dislodgement, enhance the rigidity of the treated portion of the spine, and to maximally decompress the cord. The invention permits increased distraction by blocking the kyphotic deformity introduced with marked distraction in the absence of the sleeves.

Another object is to achieve correction of deformity, stability, or anterior indirect spinal cord decompression when the posterior boney elements, or laminae, have been damaged by injury or surgically removed (laminectomy). The sleeves make it possible to achieve these objects by bridging the defect with two or more sleeves above and below the spinal defect.

The foregoing, and other objects of the invention, are provided by a surgically implanted fixation support system including at least one metal rod which is secured to a patient's spine by means of anchoring devices and at least one sleeve or spacer member. The sleeve provides an adjustable point of pressure application with regard to the amount and location of the applied force. This is accomplished by providing the sleeve, made from a biologically compatible material, with an outside diameter which is large enough to fill any gap between the metal rod and a preselected area on the patient's spine and to be in contact with the latter. To this end, the sleeves can be stocked in a number of different sizes and selected according to the degree and type of deformity or fracture. In addition, the longitudinal bore, or inside diameter, of the sleeve is approximately the same as the outside diameter of the metal rod so that the sleeve may be securely fit around the rod.

The invention provides an improved method for treating spinal deformities by surgically inserting at least one metal rod in the area of a deformed spine and attaching under compression, distraction, or both, depending on the type and extent of the deformity, a metal rod or rods to the spinal vertebrae above and below the spinal deformity, the improvement being accomplished by locating at least one sleeve member over said metal rod, with each sleeve member being of sufficient thickness and being appropriately located by the physician such that each sleeve rests in contact with and exerts a force on the spine in a direction which corrects angular and rotational deformity and stabilizes the reduction of the deformed spinal segment.

In an especially useful application of the method of this invention, surgical correction of a fractured spinal vertebrae is accomplished by the steps of attaching securing means to vertebrae located 1 to 3 interspaces above and below the fractured vertebrae, fitting a sleeve member over a metal rod, securing one end of the metal rod to one of the securing means such that the sleeve member is located substantially adjacent to the fractured vertebrae, and then securing the other end of the metal rod to the other securing means. The sleeve member is formed from a biologically compatible material and has a thickness such that the sleeve presses against the laminae, base of the spinous process and lateral masses of the fractured vertebrae when both ends of the metal rod are secured so as to correct any traumatic spinal deformity. The longitudinal bore or inside diameter of the sleeve is such that it fits firmly over the metal rod and will not be dislocated by normal body movement of the patient.

BRIEF DESCRIPTION OF THE DRAWINGS

FIG. 4 shows a compression rod with sleeves according to the invention as used to correct kyphosis.

FIG. 5 shows a distraction rod with a sleeve according to the invention at a fracture site.

FIG. 6 shows compression rods and spinal sleeves according to the invention used to stabilize replacement of a spinal section.

DESCRIPTION OF THE PREFERRED EMBODIMENTS

Figure 1:
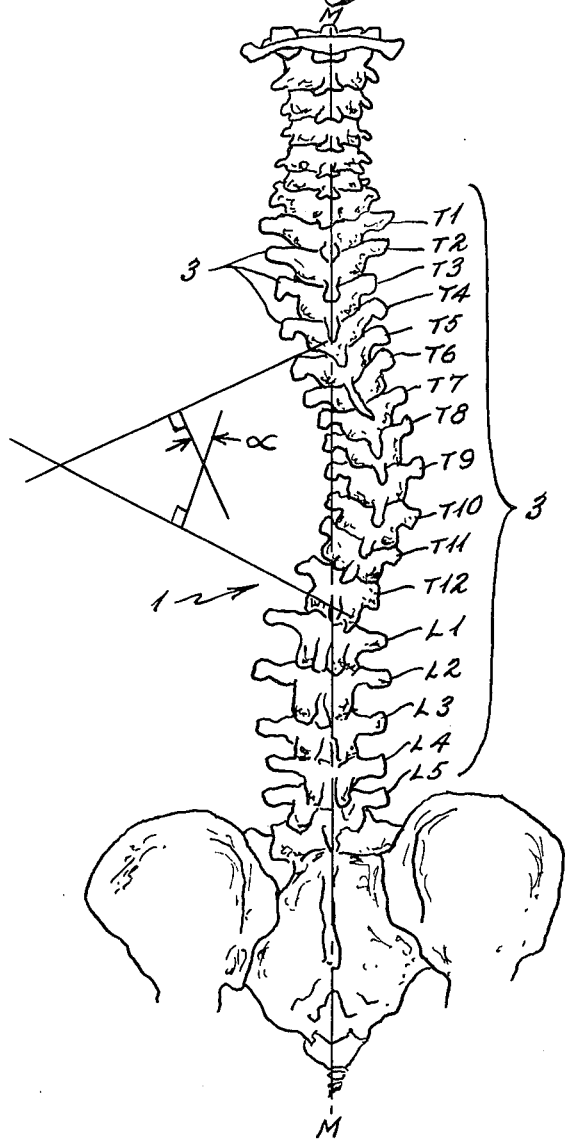
FIG. 1 is a schematic representation of a spine with idiopathic scoliosis.

FIG. 1 is an illustration of a spine of a patient suffering from scoliosis schematically represented from the rear. The spinal column 1 consists of vertebrae 3, including the vertebrae 3' designated T1-T12 and L1-L5. The patient illustrated in FIG. 1 exhibits a scoliosis involving a deviation of the vertebrae 3 to the right. The scoliotic curvature can be defined on the basis of the top vertebra T5 and the bottom vertebra T12 of the deviation, and the vertebrae T8 and T9 which are located at the peak of the curvature. It is noted that the vertebrae T5 and T12 are those which are most strongly inclined relative to the median longitudinal axis M—M of the body, while vertebrae T8 and T9 are those which are farthest from that axis. Angle $\alpha$ is thus a characteristic of the scoliotic curvature. When the scoliotic angle $\alpha$ of curvature exceeds a given limit of approximately 35°–50°, it becomes necessary to consider surgical treatment of the scoliosis. The surgical treatment is known as arthrodesis and consists of fusing together the vertebrae of the scoliotic curvature, after correcting the scoliotic curvature to the maximum possible extent by straightening and opening. Such correction can be partially accomplished prior to the operation by continuous traction of the spine 1 or by corrective plaster casts.

However, it is during surgery that the correction is completed and finalized. Typically, a solid rod with hooks is placed in the concavity of the curvature and a threaded rod with hooks is placed on the convexity of the curvature. These rods straighten the spine and maintain the correction until arthrodesis is attained by means of autogenous bone graft. The implants used most often to correct curvature during surgery are known as the Harrington distraction system and the Harrington compression system, illustrated in FIG. 2.

Figure 2:
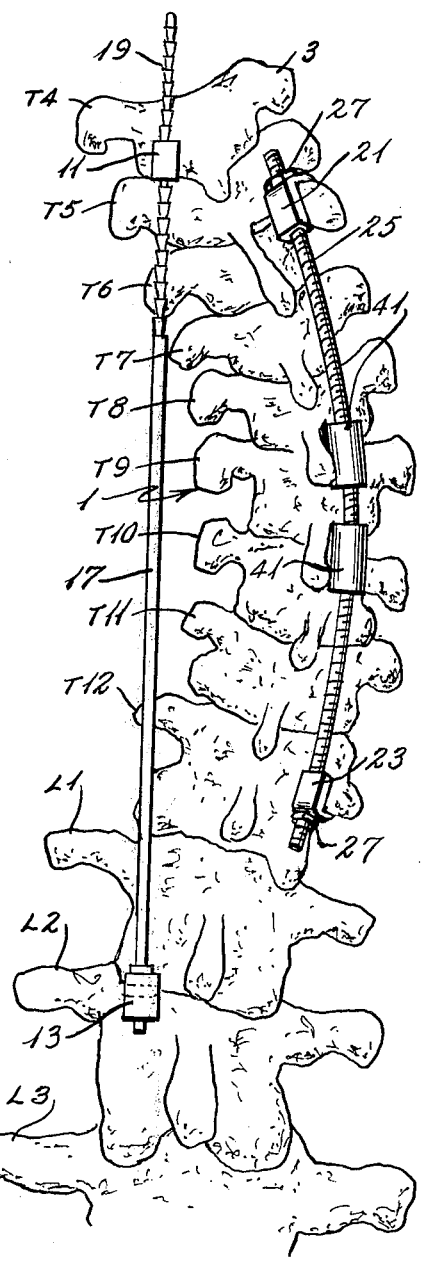
FIG. 2 shows a spinal support system using a distraction rod and a compression rod.

The distraction system of FIG. 2 includes two metallic anchoring devices 11 and 13 of the hook type, which are attached to selected ones of the vertebrae T4-T12 and L1-L2 which comprise part of the spinal column 1. A notched metal rod 17 serves as a stay and permits the spacing between the hooks 11 and 13. Such rods are available, for example, from the assignee hereof as Distraction Rods, catalogue numbers 1250-00-01/125 and 1201-01/25. One of the ends 19 of rod 17 is usually notched in such a manner as to provide a ratcheted adjustment of the distance between the hooks 11 and 13 by means of a spreading instrument. Generally, the upper anchoring device 11 is intended for fastening toward the upper end of the spine and is hooked onto a dorsal vertebra T4. Usually, the hook of the upper anchoring device 11 is directed upward and shaped in such a manner as to permit its insertion between the spinous process and a transverse process of that vertebra, between the upper and lower articular facets. The hook of the upper anchoring device 11 penetrates into the interarticular space and is supported on the vertebra T4.

Similarly, the lower anchoring device hook 13 is intended to be fastened at the lower end of the spine 1, and is often supported on a lumbar vertebra such as vertebra L2. It is contemplated that the hook 13 is directed downwardly and supported on the lamina of the lumbar vertebra L2 between the spinous process and the articular mass facet.

The compression system consists of two or more metallic anchoring devices, hooks 21 and 23, which are attached to selected lamina or transverse processes of vertebrae T4–L2 which are situated on the convex side of the scoliotic curvature. Threaded metal rod 25 serves as a stay or tension band between the hooks 21 and 23. Such rods are available from the assignee hereof, for example, as a Threaded Rod, catalogue No. 1257-00-10 Hooks 21 and 23 usually face each other and slide freely along threaded rod 25. These hooks 21, 23 are adjusted by means of hex nuts 27 so as to effect compression of the convexity of the scoliotic curvature. It is understood that more than two hooks and nuts can be used to achieve the desired amount of compression.

While the above description is generally applicable to previous surgical techniques, the present invention allows additional straightening of both angular and rotatory components of the scoliosis and improved fixation of the surgically implanted device. This is accomplished by the use of sleeve members 41 as shown in detail in FIG. 3.

Prior to securing compression rod 25 in hooks 21, 23, sleeves 41 are fitted over the rod and spaced a distance apart selected by the physician. Once the rod is secured in the hooks 21, 23, with appropriate tightening, the sleeves can be adjusted up or down so that they can rest on, and provide points of pressure application, to correct angular and rotatory deformity against the selected vertebrae; in the case of FIG. 2, sleeves 41 rest against and apply pressure to the surface of the spinous process of vertebrae T8 and T9.

If after the rods are initially secured in hooks 21, 23 it is found that either or both of the sleeves 41 is too thick to be fitted or not thick enough to fill the gap between rod 25 and the vertebrae, it is a simple matter to replace the sleeve with another of appropriate thickness.

Thus, by the application of Harrington distraction and compression systems combined with the sleeve members, the straightening of the scoliotic curvature can be effected and maintained. Vertebral arthrodesis is then achieved by exposing the posterior arches of the vertebrae 3 and attaching autogenous spongy bone with the metal rods 17, 25 left in place.

In general, the sleeve member or spacer used in this invention is fitted around a spinal fixation rod, such as a Harrington distraction or compression rod. The sleeves 41 are made of any biologically compatible material, but a non-metallic material such as high density polyethylene plastic is preferred. The sleeve may also be formed of a non-metallic material outer covering on a non-corrosive metal cylinder. Non-abrasive, carbon or other biologically compatible, biodegradable material can also be used as the sleeve material.

Figure 3:
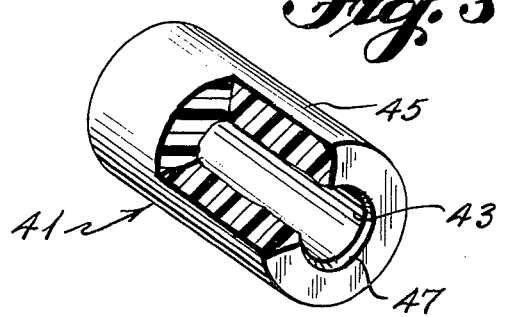
FIG. 3 shows a sleeve member according to the invention.

As shown in FIG. 3, the sleeve 41 is generally cylindrically shaped having an inner wall 43 and an outer wall 45. The inner wall 43 is dimensioned to frictionally fit around a spinal fixation rod, such as compression or distraction rods, with only a very slight clearance such as 0.127 millimeter (5/1000 in). Generally, the diameter of the longitudinal bore or opening of the sleeve ranges from about 12.48 mm to 12.64 mm, the preferred diameter of the inner wall being about 6.3 mm for most currently available spinal fixation rods. The outer wall 45 of the sleeve 41 is dimensioned to provide a secure fit of the sleeve/rod combination and the spinal structure. Thus, proper fit between a standard rod and the spinal processes of various patients and deformities is enabled by the use of one of several appropriately sized sleeves. In the preferred embodiment, the sleeves are made in at least three thicknesses (i.e., difference between outer radius and inner radius) to accommodate all regions of the thoracic and lumbar spine. For example, the sleeves can be stocked in the operating room with wall thickness of 2 mm, 4 mm and 6 mm, it being found by experience that such thicknesses can accommodate most situations normally encountered. In general, the outer diameter of the sleeve can range from about 8 mm to about 25 mm. The length of the sleeves 41 is between about 15 mm and 30 mm and is preferably about 23 mm.

Each end 47 of the inner wall 43 has a 45° chamfer for the first 0.8 mm from each end 47, it being understood that the end 47 may be chamfered as little as 0.3 mm of its length or as much as 3 mm of its length. The chamfering of the ends 47 of the inner wall 43 prevents the material of the sleeves 41 from developing frayed ends, and facilitates the placement of the sleeve 41 on the spinal rods.

In the preferred embodiment of the invention, the sleeves 41 have a radio-opaque substance added thereto. This substance provides a contrast medium for the purpose of locating the sleeves on an X-ray photograph. Barium sulfate is a preferred radio-opaque substance, with a preferred concentration ranging between 7.5% and 15% by weight, depending on the thickness of the particular sleeve. Alternatively, an X-ray wire may be included within the sleeve for radio-opacity.

While the inventive sleeves are disclosed as being used with Harrington style spinal rods, such disclosure is illustrative only. The present sleeves may be used with any style of straight rods, or with bent rods. Similarly, any anchoring means may be utilized with the rods, including suture wire or other attachment means, as well as the disclosed hooks.

FIG. 4 shows sleeves 41 inserted over a Harrington compression rod 25 as used, for example, to correct Kyphosis. The sleeves 41 are first inserted onto the rod 25, and hooks 21, 23 are then inserted on the rod. The hooks 21, 23 are secured from longitudinal movement on the rod 25 in the conventional manner by means of hex nut 27. The sleeves 41 are placed along the rod 25 so as to apply pressure against the vertebrae 3. The sleeves thus provide support and transmit a corrective force to a selected area of a patient's spinal column.

FIG. 5 shows the use of the sleeve 41 with a Harrington distraction rod 17. The sleeve 41 is fitted over the distraction rod 17. Hooks 11, 13 are secured to the distraction rod in the conventional manner by means of a collar and "C" washer (not shown).

The use of the spinal rod sleeves offers the following advantages:

1. quick and simple insertion; the desired thickness sleeve can be slipped over a standard rod which can then be inserted into standard hooks. If a thicker or thinner sleeve spacer is preferred, the original sleeve can then be removed and replaced using standard Harrington instrumentation;

2. optimum three point fixation; by selecting the right thickness sleeve, maximum correction of Kyphotic or rotatory deformity, indirect spinal cord decompression, and stability of fixation are achieved;

3. superior rotatory stability; unlike naked or bent rods, the sleeves rest against both the base of the spinous processes and lateral masses providing increased rotational stability to the injured spinal segment;

4. increased surface area of bone contact; the use of polyethylene sleeves rather than a narrow steel rod to effect the anterior pressure point helps prevent the slight loosening that can occur from pressure necrosis or laminar fracture, particularly, if there are unsuspected incomplete fractures in the lamina. This advantage is due to the increased area of contact between the rod sleeves 41 and the bone, reducing the pressure per unit area. This reduction of focal pressure, combined with the reduced stiffness of a material such as high density polyethylene relative to metal, should lessen the chance of bone pressure necrosis under the rod fixation point and resultant loosening.

It can thus be seen that the sleeves 41 provide an increased pressure-bearing area between the vertebrae 3 and the rods 17 and 25. Additionally, the sleeves 41 are larger in diameter and, being made preferably of plastic, e.g., polyethylene, are softer than the rods 17 and 25 and, therefore, are further able to distribute the forces exerted by the rods against the vertebrae 3.

The manner of use of the inventive sleeves may be better understood by the following examples.

EXAMPLE 1

Referring to FIG. 5, one of the vertebrae 3, designated 3', is indicated as having a fracture 10. The fractured spine deforms the human structure to varying extents, creating various degrees of instability and always causing pain. The more severe the injury, the more likely the possibility of spinal cord damage. When the spinal cord is injured, the ramifications can range from simple contrusion to various stages of neurological damage and finally, to complete, irreparable spinal cord injury. Some fractures are considered simple and are self-restoring, while others are more severe and cause paralysis and instability.

After general anesthesia is begun, the patient is gently placed face down and the fracture site is exposed through a posterior incision. Beginning at both ends of the incision, rather than at the mid-incision, the vertebrae 3 in the operative area are subperiosteally stripped in order to expose them with a minimum of pressure. The subperiosteal dissection is then gently extended to include the entire fracture 10. Hooks 11 and 13 are seated on those vertebrae 3' which are one to three interspaces from the fractured vertebra 3'. A Harrington distraction rod 17 with sleeve 41 is placed through the hooks 11, 13 in order to correct the spinal deformity and then provide longitudinal support for the spinal column. The distraction rod 17 has a sleeve 41 at a location adjacent to the fractured vertebra 3'. The capacity to transmit pressure to an area selected by the surgeon permits full correction of traumatic spinal deformity or dislocation. If fractured bone fragments impinge upon the spinal cord, the sleeves and method described above made it possible to decompress the spinal cord indirectly. These sleeves also provide support for the fractured vertebra 3' without necessitating bending of the distraction rod 17 even in the lumbar regions of the spine.

It can be readily seen that with the Harrington distraction rod 17 in a straight rather than a bent configuration, the rod will not tend to rotate, and that even if the rod were rotated, no problems would result.

EXAMPLE 2

In another example of the use of rod sleeves in conjunction with a spinal rod assembly to increase the stability of the spine, a section of the spinal column 1 had to be resected to insure that all of a malignant tumor was removed. The resected portions included vertebrae L-1, L-2 and L-3, as well as part of T-12. This left the spinal cord, as well as the inferior vena cave and abdominal aorta, exposed to injury from movement. A spine support section, shown in FIG. 6, was inserted in place of the missing vertebrae, as shown in FIG. 7.

As can be seen in FIG. 6, the artificial spinal section, denoted as 61, is made from a metal body 63 into which two retractable metal projections 65 are inserted. A metal alloy of iron, chrome, cobalt and molybdenum is used. The body 63 has top and bottom end portions 67, 69 which connect to a mid-portion 71. The end portions 67, 69 are generally disc-shaped and are formed integrally with the mid-portion 71. The mid-portion 71 is generally in the form of a cylinder section with an outer wall 73 which is a continuation of the surfaces of the top and bottom sections 67, 69. Therefore, it can be seen that the top section 67 is fixed in relation to the bottom section 69 by the cylinder section 73. However, additional support is provided by two longitudinal struts 74 which extend between the end portions 67, 69 opposite the mid-portion 71. Bores 75 within the end portions 67, 69 receives the projections 65 in sliding relation therein. When desired, the projections 65 are prevented from sliding in the bores 75 by conventional fasteners such as screws 77. In the preferred embodiment recesses 79 are provided in the ends 67, 69 in order to receive the heads of the screws 77 so that the screws 77 do not protrude beyond the artificial spinal section 61.

The artificial spinal section 61 is inserted in a spinal column 81. Prepared bores 83 are bored into the body 85 of those vertebrae 3 which are adjacent to the resected section of the spine. The prepared bores 83 are dimensioned so as to receive the projections 65 therein. The artificial spinal section 61 is then inserted in place of the resected section 87 of the spinal column 81. The retractable rods 65 are inserted into the prepared bores 83 and secured in place by means of methyl methacrylate cement and the fasteners 77.

The repaired spine is further stabilized by means of two Harrington compression rods 25. Hooks 21, 23 are secured at each end of the rods 25, and two sleeves 41 are placed over each rod between the adjacent to the hooks 21, 23. The rods counteract forward bending forces crossing the artificial spinal segments. The sleeves fit into the natural contour of the laminae to provide rotatory stability.

Corticocancellous bone grafts taken from the patient's right ilium are placed along the body of the artificial section. A metal tension band 95 may also be used and is fixed by fasteners 97 so as to connect the vertebrae 3 above the artificial spinal section 61 with the vertebrae 3 below the artificial spinal section 61.

Thus, it can be seen that the Harrington rods 25 and the spinal sleeves 41 can be used in connection with the artificial spinal section 61 in order to increase the stability of the spinal column.

Other examples of spinal sleeve uses include correction of rotational deformity in scoliosis surgery by applying anterior force to the posteriorly rotated side of the spinal column, correction of Kyphotic deformities in such conditions as Scheurman's Disease, and use with compression rods in spinal injury to maximize correction of traumatic deformity.

From the preceding examples, it can be seen that the sleeves 41 are useful in providing additional corrective pressure and support when used in conjunction with Harrington rods 17, 25. It has been shown, for example, that the use of a Harrington distraction rod with a sleeve 41 has provided an improved repair for a fractured spinal column. It has also been shown that the use of a Harrington compression rod with sleeves 41 has provided sufficient stability to a spinal column 1 to enable the replacement of a section of the spinal column. However, these examples are meant to illustrate, and not to limit the use of the inventive devices to those specific repairs. Nor are the examples intended to limit the use of sleeves 41 to Harrington rods. For example, the improved support provided by this combination will be useful in the correction of scoliotic, rotatory, Kyphotic and other deformities of the spine. Furthermore, as previously discussed, the sleeves 41 may be used in connection with spinal rods other than Harrington type, and with anchoring means other than the hooks illustratively shown in the foregoing disclosure. Accordingly, it is the inventor's intention to disclose an improved method of and apparatus for applying force to a spinal column using rod sleeves or spacers to apply pressure to vertebrae selected by the physician and to increase the stability of the spine.

What is claimed is:

1. A surgically implanted spinal fixation support system comprising at least one metal rod, a plurality of anchoring devices for securing said metal rod to a patient's spine, and at least one sleeve member fitting around the rod, disposed between the anchoring devices, the sleeve members not associated with any anchoring devices for providing an adjustable area of pressure application to the spine, the sleeve comprising a biologically compatible non-metal material and having a longitudinal bore therethrough, the bore being of a substantially equal diameter throughout its length, the bore being approximately the outside diameter of said rod and for the purpose of fitting the sleeve around the rod and an outside diameter which is small enough in size so as to enable the rod to be surgically fixed with the sleeves to the spinal column of a patient and the thickness of said sleeve being large enough to make bone contact with the spine. to hold the spine in a normal or anatomic position.

2. The spinal fixation support system of claim 1 wherein said sleeves are provided with at least three different outside diameters to allow the physician to select from among sleeves having nominal thicknesses of 2 mm, 4 mm and 6 mm.

3. The spinal fixation support system of claim 1 wherein the sleeve has an inside diameter such that the sleeve will not move freely when placed over said metal rod and an outside diameter ranging from about 8 mm to about 25 mm.

4. The spinal fixation support system of claim 1 wherein chamfers are provided at each end of the longitudinal bore, the chamfer being approximately 45° and extending no less then 0.3 mm and not more than 3 mm from each end of the bore.

5. The spinal fixation support system of claim 1 wherein the sleeve member has a length in the direction of the bore which is not less than 15 mm and not more than 30 mm.

6. The spinal fixation support system of claim 1 wherein the sleeve is adapted for use with a Harrington spinal system of the type wherein at least one Harrington rod is used to apply a force to the spine, the Harrington rod being either a Harrington compression rod or a Harrington distraction rod.

7. The spinal fixation support system of claim 1 wherein:
(a) the sleeve member has a length in the direction of the bore which is not less than 15 mm and not more than 30 mm;
(b) the longitudinal bore has a diameter which is between 6.24 and 6.32 mm; and,
(c) the outside diameter of the sleeve is between 8 mm and 25 mm.

8. The spinal fixation support system of claim 7 wherein chamfers are provided at each end of the longitudinal bore, the chamfer being approximately 45° and extending no less than 0.3 mm and not more than 3 mm from each end of the bore.

9. The spinal fixation support system of claim 7 wherein the biologically compatible material of said sleeve member is high-density polyethylene plastic or carbon or metal covered with plastic, carbon, or other material softer than metal.

10. The spinal fixation support system of claim 9 wherein the plastic further comprises a radio-opaque substance.

11. The spinal fixation support system of claim 10 wherein the radio-opaque substance is barium sulfate and the barium sulfate is in a concentration in the plastic material of between 4 and 15% by weight.

12. The spinal fixation support system of claim 9 wherein the plastic sleeve further comprises an X-ray wire so that observation of said sleeve by X-ray photography can be facilitated.

13. The spinal fixation support system of claim 1 wherein the anchoring devices are metal members in which one end is provided with an opening which receives the rod and a second end is provided with a hook-like projection which engages a vertebrae of the spine.

14. The spinal fixation support system of claim 13 wherein the rod is provided with means for preventing movement of the anchoring devices longitudinally away from each other, thereby exerting a compressive force on the spine.

15. The spinal fixation support system of claim 13 wherein the rod is provided with means for preventing movement of the anchoring devices longitudinally toward each other, thereby exerting a distractive force on the spine.

16. The spinal fixation support system of claim 13 wherein each of said rods is provided with means for preventing longitudinal movement of the anchoring devices on the rod.

17. The spinal fixation support system of claim 16 wherein one of said rods is externally threaded, and wherein the means for preventing longitudinal movement of the anchoring devices on the threaded rod comprises internally threaded nuts mounted on the threaded rod.

* * * * *